United States Patent [19]

Choi

[11] 4,417,889
[45] Nov. 29, 1983

[54] DEVICE FOR A PORTABLE AUTOMATIC SYRINGE

[76] Inventor: Soo-Bong Choi, 47-3, 4-Ka, Namdaemoon-Ro, Joong-Ku, Seoul, Rep. of Korea

[21] Appl. No.: 299,951

[22] Filed: Sep. 8, 1981

[30] Foreign Application Priority Data

Dec. 31, 1980 [KR] Rep. of Korea ............... 80-5060
Dec. 31, 1980 [KR] Rep. of Korea ............ 80-8520[U]
Dec. 31, 1980 [KR] Rep. of Korea ............ 80-8521[U]

[51] Int. Cl.³ ........................................... A61M 5/00
[52] U.S. Cl. ................................................ 604/246
[58] Field of Search .......... 128/214 E, 214 F, 218 A, 128/DIG. 12, DIG. 13

[56] References Cited

U.S. PATENT DOCUMENTS 4,111,198  9/1978  Marx et al. ............... 128/214 E
4,168,707  9/1979  Douvas et al. ............ 128/DIG. 13
4,173,224 11/1979  Marx et al. ............... 128/214 E
4,217,993  8/1980  Jess et al. ................. 128/214 E
4,231,366 11/1980  Schael ...................... 128/214 E Primary Examiner—John D. Yasko
Attorney, Agent, or Firm—Haight & Associates

[57] ABSTRACT

The disclosure relates to a safety device for a portable automatic syringe. On injection for a diabetic this new device can not only prolong the injection time, but also timely and favorably control the injection amount.

Furthermore it is so compact that a patient can carry along in safety.

In other words, it is an insulin automatic syringe developed in a particular way, especially for use by a diabetic. Generally speaking, if a patient employs this device, he is in a position to easily manage himself and assure injection of the insulin injection which is prescribed. This device is provided with fixed number switches as a safety feature to prevent excess injection.

At the same time, the device is also provided with a control unit which protects against repetitive injection even if he inadvertently performs a repetitive injection.

4 Claims, 5 Drawing Figures

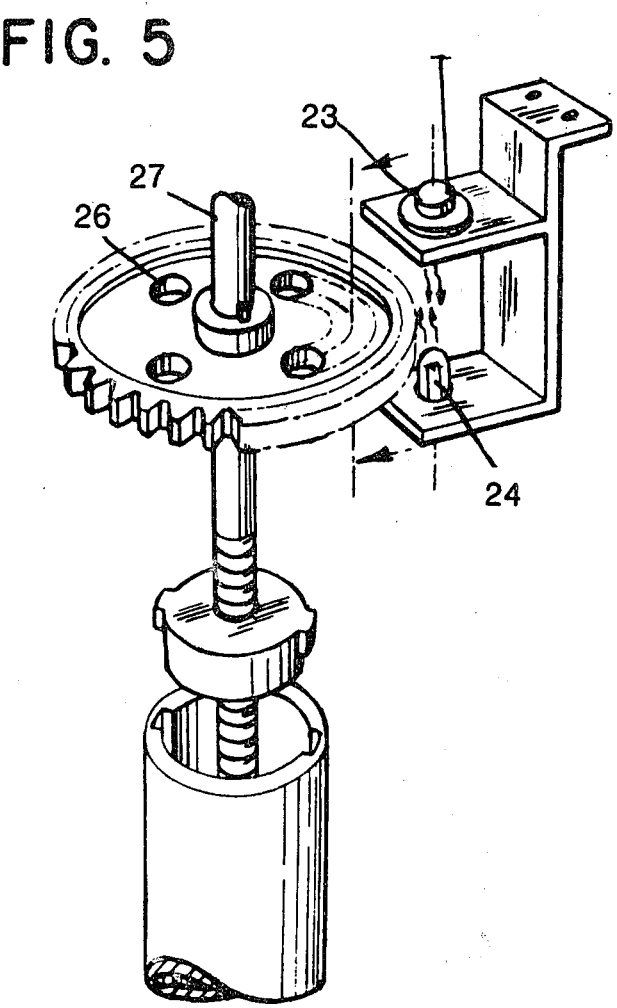
FIG. 5
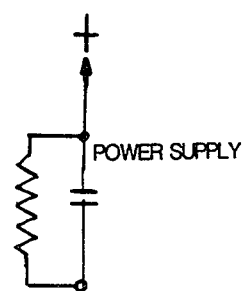
FIG. 4
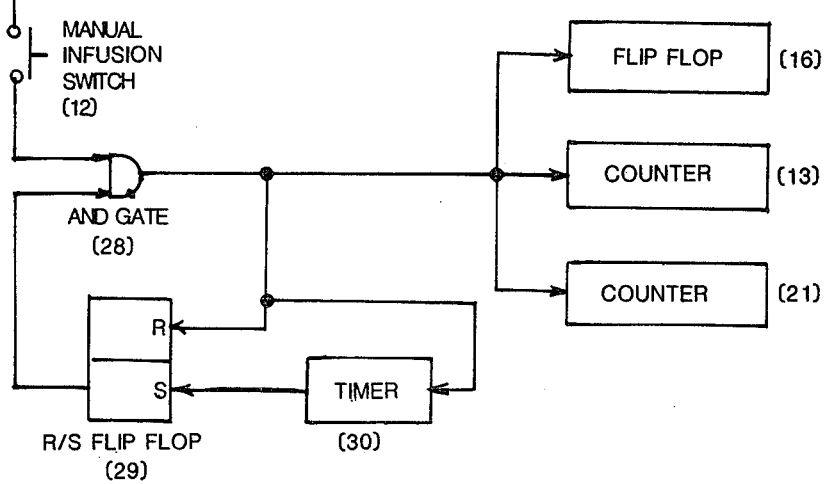

DEVICE FOR A PORTABLE AUTOMATIC SYRINGE

An automatic syringe published as a laying-open application for utility model series No. 52-3292 in Japan has been introduced into the world. However, this device is of the so-called analogue type which can only allow intermittently adjusting the required amount of injection by means of manually operating the variable resistor.

The analogue type automatic syringe has inherent disadvantages in allowing neither accurate injections as needed nor automatic adjustments of injection amount. The new device of the present invention has two oscillators, one of which is for timers and the other is for counter units that work regularly or intermittently to adjust the most favorable amount of injection by means of digitally setting them in advance. Therefore, this can be called a type of portable automatic-syringe device.

Since this device is used for injections to cure a disease of the human body and requires high accuracy and safety in terms of medicine, it is provided with fixed number switches for safety, control units against repetitive injection, and an excess-injection preventitive unit.

In the drawings, wherein like characters of reference pertain to like parts throughout the several figures;

FIG. 4 is a diagram of a control unit to prevent repetitive injections; and

FIG. 5 is a vertical section of a perspective of a unit to prevent excess-injection.

Figure 2:
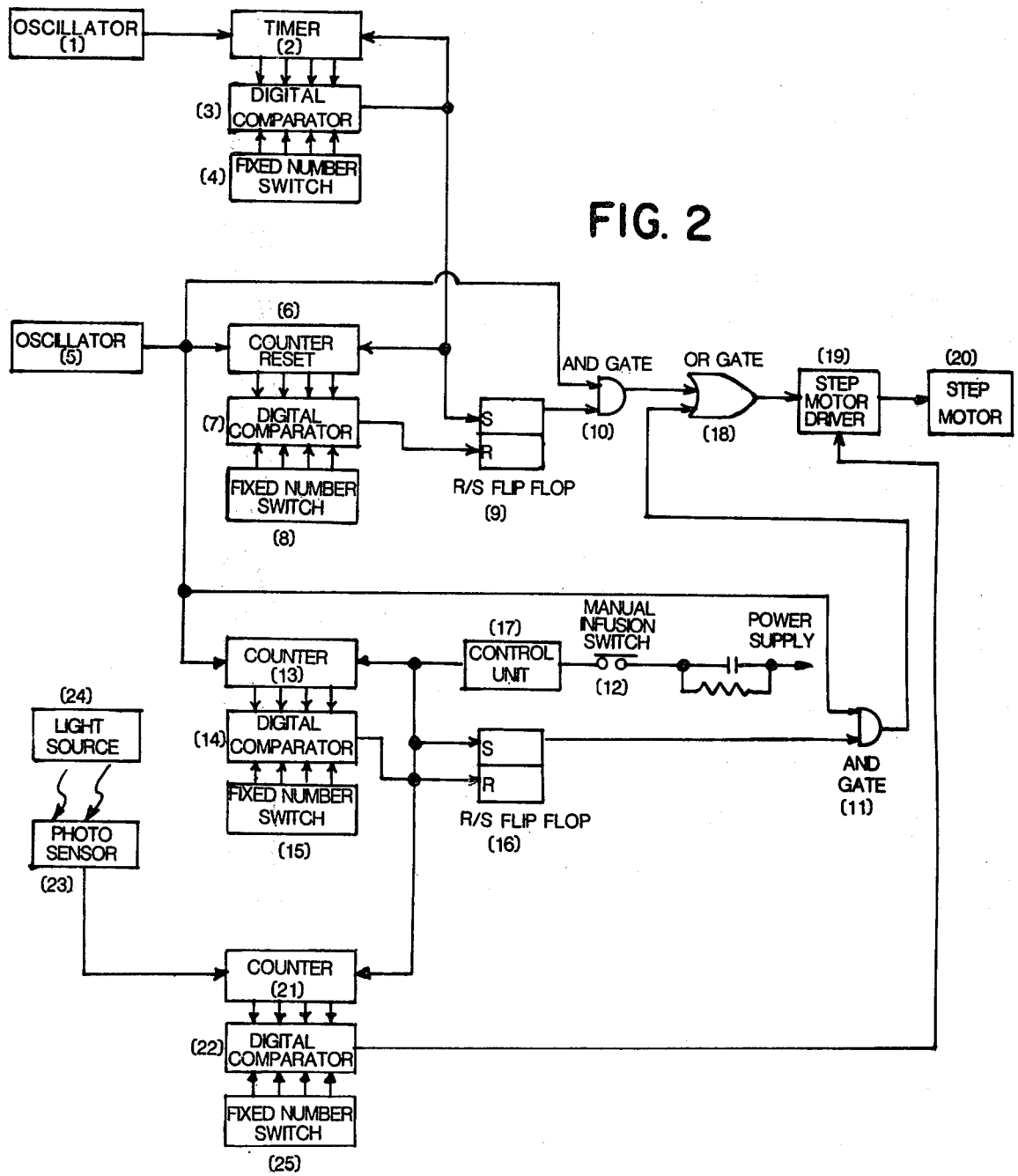
FIG. 2 is a electronic circuit diagram.

Referring to FIG. 2, oscillator (1) connects to timer (2) and the output of digital comparator (3) connects to the timer (2), counter (6) and flip-flop (9). Another oscillator (5) connects to the counter (6), AND gate (10)(11) and counter (13). The output of digital comparator (14) resets the flip-flop (9) and the output of the digital comparator (14) resets the flip-flop (16). A control unit against repetitive injection (17) is provided between manual infusion switch (12) and the counter (13). The output of the control unit (17) connects to the counters (13) and (21) and the flip-flop (16). The output of digital comparator (22) connects to a step motor driver (19) to stop step motor (20). The output of the flip-flop (16) is an input to the AND gate (11) which connects to OR gate (18).

The step motor driver (19) is used for driving the step motor (20).

Figure 3:
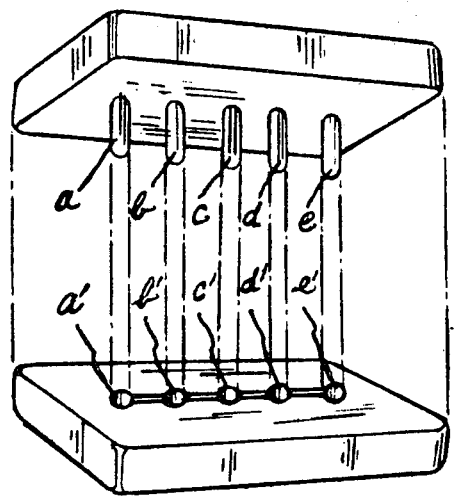
FIG. 3 is a side elevation of fixed number switches for safety.

Each of the fixed number switches (4), (8), (15) and (25) has five protruding insert bars and adaptors as indicated in FIG. 3.

As best seen in FIG. 5, several holes (26) are made through the gear plate. A gear shaft (27) is fitted on the gear plate. And the piston plate is movably fitted in the gear shaft (27), the most part of which is screwed. A innovative combination of a light source (24) and a photo sensor (23) is attached to the lower and upper parts of a fixture as shown in FIG. 5.

Figure 1:
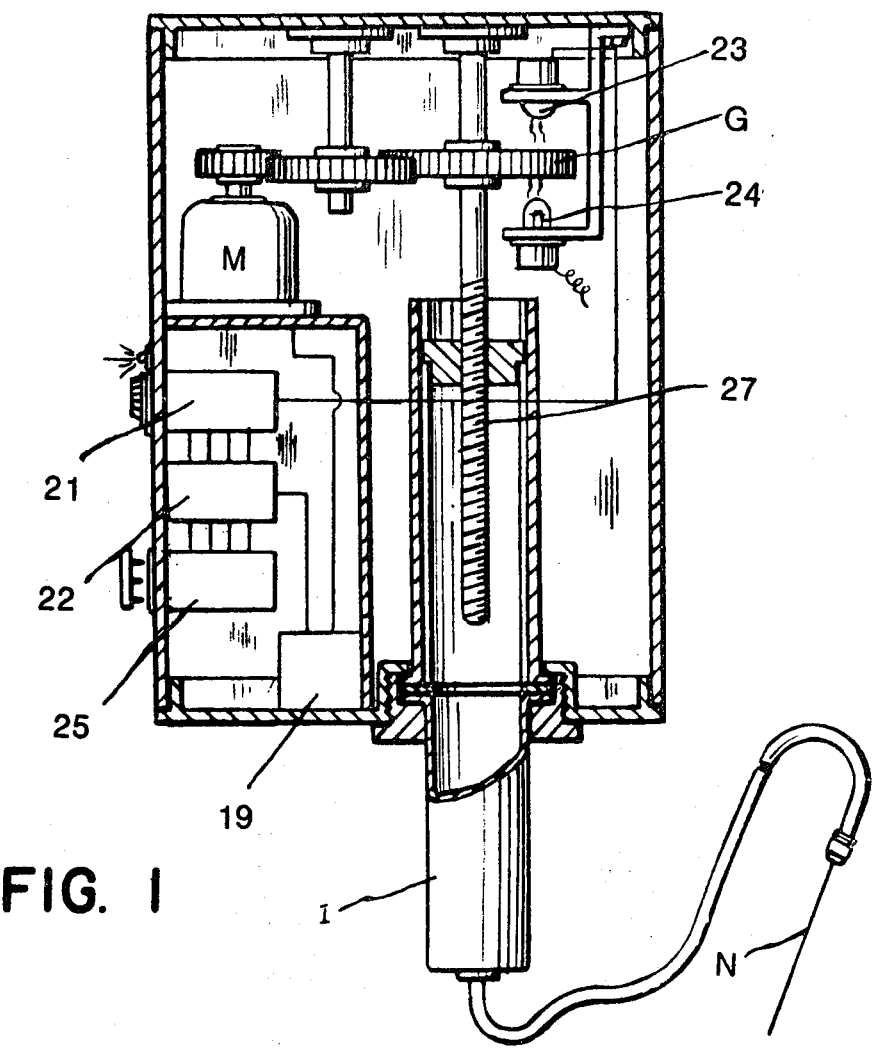
FIG. 1 is a vertical section through the treating means.

The overall assembly is shown in FIG. 1, wherein the following symbols are used: "G" for gear, "M" for motor, "I" for syringe and "N" for injection needle.

The following explanation will make more understandable the functions and the effectiveness of the operation process with the new device of this invention.

Referring again to FIG. 2, the digital comparator (3) compares the output of the timer (2) with the value of the fixed number switch (4) in which the prescribed period of time has been set in advance on the basis of the physical condition of a patient. The timer (2) counts pulses from the system oscillator (1) e.g. progressing by sixties at every second. When the output of the timer (2) and the value of the fixed number switch (4) coincide, one pulse comes out of the digital comparator (3) for resetting the timer (2) and setting the flip-flop (9).

The counter (6) counts pulses from the oscillator (5) which has been designed for oscillating slower than the oscillator (1) on the decimal system. The digital comparator (7) compares the output of the counter (6) with the value of the fixed number switch (8) in which the prescribed amount of injections has been set in advance on the basis of the physical condition of the patient. When the output of the counter (6) and the value of the fixed number switch (8) coincide, one pulse comes out of the digital comparator (7) for resetting both counter (6) and flip-flop (9).

If the flip-flop (9) sets, the AND gate (10) enables the pulse signals from the oscillator (5) to pass through to the OR gate (18) and if the flip-flop (9) resets, the AND gate (10) disables thepulse signals from passing through the OR gate (18).

The combined circuit of the counter (13), the digital comparator (14) and the fixed number switch (15) is connected similarly to the above mentioned combination of the counter (6), digital comparator (7) and the fixed number switch (8). However, in this case the amount of injections preset by the fixed number switch (15) is normally greater than the amount set by the fixed number switch (8) to give more insulin injections at special times, for instance, meal time. In this connection, when a patient pushes the manual infusion switch (12), the counter (13) resets and the flip-flop (16) sets, so that the step motor starts through the OR gate (18) and the AND gate (11) which receives the pulse signals from the oscillator (5).

Explaining the control unit against repetitive injection, (see FIG. 4), an AND gate (28), a flip-flop (29) and a timer (30) are added between the manual infusion switch (12) and the above mentioned systems such as (11) (12) (13) (14) (15) (16), which is referred to herein as the increased amount injection system. When a patient pushes the manual infusion switch (12), the AND gate (18) immediately sets the flip-flop (29) and resets the timer (30) at the same time.

The flip-flop (29) is only allowed to reset after a prescribed period of time which is counted by the timer (30) so that repetitive-injections are prevented even if the manual infusion switch (12) is untimely pushed by the patient's mistake in the interval during the prescribed period of time.

A step motor (20) is connected with the transmission gears, one of which is a cog gear mounted on a screw gear shaft of the syringe (I). When this cog gear shaft is driven by the step motor (20), the piston plate led along with the screw pushes the piston downward to dispense the prescribed amount of injection to the human body.

The fixed number switches (4), (8), (15) and (25) are different from existing thumb wheel switches, which are rotary types. Ech of the fixed number switches has five protruding insert bars (a) (b) (c) (d) (e) and adaptors (a') (b') (c') (d') (e') as mentioned. These five protruding insert bars are internally connected to form various combinations of connections. The female adaptors are installed into the case of the automatic syringe. Accordingly, since the fixed number switches cannot be easily disassembled and changed, it can be seen that the prescribed amount of injection can be assuredly give to the patient.

The photo sensor (23) is aimed to receive intermittent beams of light from source (24) which come through the several holes (26) on the gear plate. When the number of pulses counted by the counter (21) through this photo sensor (23) is greater than the value of fixed number switch (25), a signal comes out of the digital comparator (22) to interrupt the step motor driver (19) with an alarm. Accordingly, excess injection can be safely prevented by the above configuration.

I claim:

1. In a portable automatic insulin injection syringe pump device including a step motor and a motor driving circuit, the improvement comprising:
    (a) means for setting an injection time period comprising a first oscillator for producing pulses, a timer connected to said oscillator to count said pulses, a first fixed number switch for presetting a desired injection time, and a first digital comparator for comparing the outout of said timer with said first switch;
    (b) means for injecting a prescribed insulin dosage comprising a second oscillator for producing pulses slower than said first oscillator, a counter for counting said pulses, a second fixed number switch for presetting the prescribed amount of injections, and a second digital comparator for comparing the output of said counter and said second switch;
    (c) means for injecting an increased insulin dosage comprising a third oscillator for producing pulses, a counter for counting said pulses, a third fixed number switch for presetting the prescribed amount of injections, and a third digital comparator for comparing the output of said counter and said third switch, wherein said third fixed number switch is preset to permit delivery of an increased amount of insulin;
    (d) a control unit for preventing repetitive injection of increased amounts of insulin; and
    (e) means for preventing excess injection comprising a light source, a photosensor, counter for counting the number of light pulses, a fourth fixed number switch, and a fourth digital comparator.

2. A device as defined in claim 1, wherein the fixed number switches comprise respectively male parts having a plurality of protruding insert bars and female adaptors having a plurality of holes adapted to electrically connect with said bars, said protruding insert bars being internally connected to each other to form various combinations of connections so that the fixed number switches cannot be easily disassembled and changed by a user, whereby the prescribed amount of injection is assured.

3. A device as defined in claim 1, wherein said control unit for preventing repetitive injection comprises a manual infusion switch connected to an AND gate, a flip flop and a timer such that, when a user pushes the manual infusion switch, said AND gate enables simultaneous, immediate resetting of said flip flop and timer, whereby repetitive injections are prevented even if the manual infusion switch is untimely pushed by a patient's mistake during a prescribed time period interval.

4. A device as defined in claim 1, wherein said means for preventing excess injection comprises a light source, a photosensor for receiving intermittent beams of said source passing through a plurality of holes on a gear plate, a counter for counting the number of pulses received by said photosensor, a digital comparator for comparing the value of said fixed number switch with the pulses counted by said counter, and a fixed number switch for presetting a prescribed amount of injection such that when the number of pulses counted by said photosensor is greater than the value of said switch, the step motor driver interrupts by ringing an alarm.

* * * * *